(12) United States Patent
Archambault et al.

(10) Patent No.: US 11,294,076 B2
(45) Date of Patent: Apr. 5, 2022

(54) DEFORMABLE DOSIMETER

(71) Applicants: Louis Archambault, Québec (CA); Luc Beaulieu, Québec (CA); Émily Cloutier, Québec (CA)

(72) Inventors: Louis Archambault, Québec (CA); Luc Beaulieu, Québec (CA); Émily Cloutier, Québec (CA)

(73) Assignee: UNIVERSITÉ LAVAL, Québec (CA)

( * ) Notice: Subject to any disclaimer, the term of this patent is extended or adjusted under 35 U.S.C. 154(b) by 0 days.

(21) Appl. No.: 16/541,372

(22) Filed: Aug. 15, 2019

(65) Prior Publication Data

US 2020/0057165 A1    Feb. 20, 2020

Related U.S. Application Data

(60) Provisional application No. 62/764,650, filed on Aug. 15, 2018.

(51) Int. Cl.
*G01T 1/10*      (2006.01)
*A61B 6/00*      (2006.01)

(52) U.S. Cl.
CPC ............... *G01T 1/10* (2013.01); *A61B 6/583* (2013.01)

(58) Field of Classification Search
CPC .......... G01T 1/10; A61B 6/583; A61B 6/542; A61N 5/1048; A61N 5/1049
See application file for complete search history.

(56) References Cited

U.S. PATENT DOCUMENTS

| | | | |
|---|---|---|---|
| 2002/0131552 A1* | 9/2002 | Nishizawa | A61B 6/583 378/65 |
| 2008/0298540 A1* | 12/2008 | Serban | G09B 23/32 378/18 |
| 2012/0330083 A1* | 12/2012 | Aitkenhead | A61N 5/1071 600/1 |
| 2019/0239846 A1* | 8/2019 | Sawant | A61B 6/487 |
| 2019/0329072 A1* | 10/2019 | Magro | G01T 1/02 |

FOREIGN PATENT DOCUMENTS

| | | | | |
|---|---|---|---|---|
| WO | WO-2014022480 A1 * | 2/2014 | ............... | G01T 1/11 |
| WO | WO-2015168729 A1 * | 11/2015 | ............... | G01T 1/06 |

* cited by examiner

*Primary Examiner* — Christine S. Kim
(74) *Attorney, Agent, or Firm* — Bereskin & Parr LLP/S.E.N.C.R.L., s.r.l.

(57) ABSTRACT

A radiation dosimeter for measuring radiation dose within a region includes a structure having a scintillating material that emits light when exposed to radiation. Deformable radio-luminescent elements are located within the structure and configured to generate optical energy in response to irradiation.

18 Claims, 12 Drawing Sheets

DEFORMABLE DOSIMETER

FIELD OF THE DISCLOSURE

The present disclosure relates to a deformable dosimeter, and in particular a deformable dosimeter for providing real-time measurements of a radiation dose while simulating shape and/or deformation of a patient's organs and/or anatomical regions.

BACKGROUND OF THE DISCLOSURE

Radiation therapy uses ionizing radiation to treat or destroy cancerous tumours and lesions. The damage to tumour cells from the radiation is related to the absorbed dose (i.e., energy absorbed from ionizing radiation per unit mass). Therefore increasing the dose to the tumour increases the number of treated or destroyed cancer cells. However, as higher dose levels may also affect healthy tissue and other structures surrounding the tumour, the amount of ionizing radiation used must be controlled to provide as high as possible a dose to the tumour site whilst avoiding or at least reducing damage to the surrounding healthy tissues.

When irradiating a target region such as an organ, it is desirable to simulate and obtain multiple dose points in the target region for 2D or 3D reconstruction of the radiation dose. It is also desirable to evaluate effect of the irradiation on surrounding regions. Furthermore, it is desirable to simulate various deformation scenarios of a target region such as volume, shape and/or position changes and any discontinuities while the target region is being irradiated.

SUMMARY OF THE DISCLOSURE

According to one aspect, there is disclosed a radiation dosimeter for real-time measurements of a radiation dose within a region, wherein the radiation dosimeter comprises:
  a phantom; and
  at least one deformable radio-luminescent element located within the phantom and configured to generate optical energy in response to irradiation.

In some cases, the phantom may be deformable.

According to one aspect, there is a disclosed a radiation dosimeter for real-time measurements of a radiation dose within a region, wherein the radiation dosimeter comprises:
  a deformable phantom; and
  at least one radio-luminescent element located within the phantom and configured to generate optical energy in response to irradiation.

In some cases, the radio-luminescent element may be deformable.

In some cases, a plurality of deformable radio-luminescent elements may be located within the phantom for detecting the radiation dose at multiple points in the region.

In some cases, the plurality of deformable radio-luminescent elements may be contiguous.

In some cases, one or more of the plurality of deformable radio-luminescent elements have different optical emission spectra.

In some cases, at least one of the radio-luminescent elements includes water and/or tissue equivalent materials.

According to another aspect, there is disclosed a radiation dosimeter for real-time measurements of a radiation dose within a region, wherein the radiation dosimeter includes:
  a structure; and
  at least one deformable radio-luminescent element located within the structure and configured to generate optical energy in response to irradiation. In some cases, the structure may include a scintillating material, wherein the scintillating material emits light when exposed to radiation In some cases, the structure may be deformable.

In some cases, a plurality of deformable radio-luminescent elements may be located within the structure for detecting the radiation dose at multiple points in the region.

In some cases, the plurality of deformable radio-luminescent elements are contiguous.

In some cases, the plurality of deformable radio-luminescent elements have different optical emission spectra.

In some cases, at least one of the radio-luminescent elements comprises water and/or tissue equivalent materials.

In some cases, the phantom, the structure or the radio-luminescent elements is configured to take a shape of an organ and/or an anatomical region.

In some cases, the anatomical region comprises one of: a thorax, a neck, a head, and a pelvis.

According to another aspect, there is disclosed a radiation system for real-time measurements of a radiation dose within a region, including:
  a phantom;
  a plurality of deformable radio-luminescent elements located within the phantom and configured to generate optical energy in response to irradiation at multiple points in the region;
  a first actuator configured to deform at least one of the deformable radio-luminescent elements; and
  a processor configured to receive radiation data from the plurality of deformable radio-luminescent elements.

In some cases, the phantom includes a deformable material and wherein a second actuator is configured to deform the phantom.

In some cases, the radiation data are recorded while at least one of the plurality of deformable radio-luminescent elements is being deformed and/or irradiated.

In some cases, the radiation data are recorded from different angles.

In some cases, the radiation data allow a tomographic reconstruction of the radiation dose for each voxel of the region.

In some cases, the plurality of deformable radio-luminescent elements have different optical emission spectra.

In some cases, at least one of the radio-luminescent elements includes water and/or tissue equivalent materials.

According to another aspect, there is disclosed a radiation system for real-time measurements of a radiation dose within a region, including:
  a structure having a scintillating material;
  a plurality of deformable radio-luminescent element located within the structure and configured to generate optical energy in response to irradiation at multiple points in the region;
  a first actuator configured to deform at least one of the deformable radio-luminescent elements; and
  a processor configured to receive radiation data from the scintillating material and/or the plurality of deformable radio-luminescent elements.

In some cases, the scintillating material of the structure is deformable and wherein a second actuator is configured to deform the structure.

In some cases, the radiation data are recorded while the scintillating material of the structure and/or the at least one of the plurality of deformable radio-luminescent elements is/are being deformed and/or irradiated.

In some cases, the radiation data are recorded from different angles.

In some cases, the radiation data allow a tomographic reconstruction of the radiation dose for each voxel of the region.

In some cases, the plurality of deformable radio-luminescent elements have different optical emission spectra.

In some cases, at least one of the radio-luminescent elements includes water and/or tissue equivalent materials.

According to another aspect, there is disclosed a method for real-time measurements of a radiation dose in a dosimeter within a region, including:
- deforming a phantom or deforming one or more deformable radio-luminescent elements located within the phantom and configured to generate optical energy in response to irradiation;
- irradiating the one or more deformable radio-luminescent elements using a radiation source; and
- measuring the radiation dose in the one or more deformable radio-luminescent elements.

In some cases, the method further includes measuring the radiation dose from different angles.

In some cases, the method further includes displaying a tomographic reconstruction of the radiation dose for each voxel of the region.

In some cases, the deforming step comprises deforming the phantom and/or the one or more deformable radio-luminescent elements to simulate a deformation of an organ or an anatomical region.

In some cases, the anatomical region includes one of: a thorax, a neck, a head, and a pelvis.

According to another aspect, there is disclosed a method for real-time measurements of a radiation dose in a dosimeter within a region, including:
- deforming a structure having a scintillating material, wherein the scintillating material emits light when exposed to radiation;
- deforming one or more deformable radio-luminescent elements located within the structure and configured to generate optical energy in response to irradiation;
- irradiating the structure or the one or more deformable radio-luminescent elements using a radiation source; and
- measuring the radiation dose in the structure or the one or more deformable radio-luminescent elements.

In some cases, the method further includes measuring the radiation dose from different angles.

In some cases, the method further includes displaying a tomographic reconstruction of the radiation dose for each voxel of the region.

In some cases, the deforming step includes deforming the structure and/or the one or more deformable radio-luminescent elements to simulate a deformation of an anatomical region.

In some cases, the anatomical region includes one of: a thorax, a neck, a head, and a pelvis.

DETAILED DESCRIPTION OF THE DISCLOSURE

Figure 1:
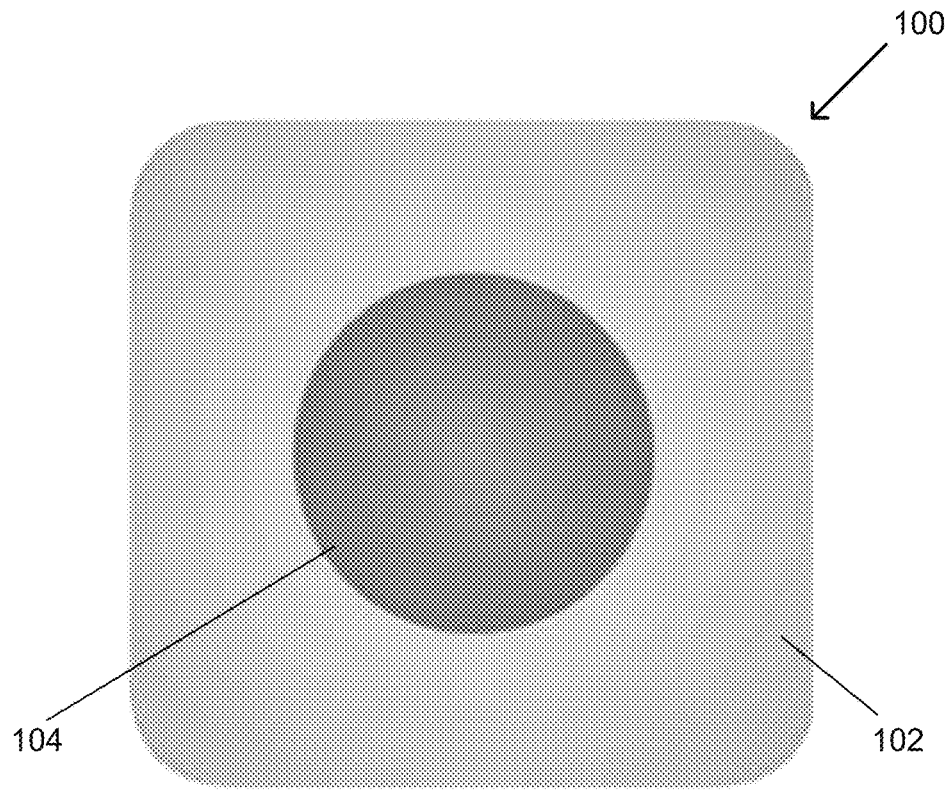
FIG. 1 shows a radiation dosimeter according to one example.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

As used in the present disclosure, the singular forms "a", "an" and "the" include plural references unless the content clearly dictates otherwise. Thus for example, a radiation dosimeter containing "a radio-luminescent element" includes a mixture of two or more radio-luminescent elements. It should also be noted that the term "or" is generally employed in its sense including "and/or" unless the content clearly dictates otherwise.

As used in the present disclosure, the terms "deform" and "deformation" mean displacement, rotation, change in shape or form, change in volume, and/or or any combination of these. The change in shape can be an outward expansion or can be any other change in shape, such as to change from a straightened to a non-straightened (e.g., curved or wavy) shape. The deformation can be measured in a two-dimension space using a two-dimensional coordinate system (e.g. x-y axes). The change in shape can be measured in a three-dimensional coordinate system (e.g. x-y-z axes). For example, the shape change can occur in a variety of manners. For example, the terms "deforming an object" mean that the object, which can initially be round, may change its shape and/or volume to e.g. oval due to a pressure force, which is brought onto the object. When the pressure force deforms the object, the pressure force may be applied over a contact surface of the object.

As used in the present disclosure, the term "real-time measurements of radiation" means that the effect of radiation and/or the dose of radiation are measured rapidly, for example, in less than five minutes. "Near-real-time" means that the effect of radiation is measured in less than twenty minutes.

As used in the present disclosure, the term "organ" means a collection of tissues that perform a specific function, such as the prostate, kidney, ovary or eye. The term "organ system" refers to a group of organs that work together to perform one or more functions. Examples of organs include: the kidneys, ureters, bladder and urethra (which are parts of the urinary system); the penis, testicles, seminal vesicles and prostate (which are parts of the male reproductive system); the vagina, cervix, uterus, fallopian tubes, ovaries and breasts (which are parts of the female reproductive system); the adrenal glands, ovaries, testicles (testes), pituitary gland, thyroid gland, parathyroid glands and the pancreas (which are parts of the endocrine system); the nose, mouth, windpipe (trachea), bronchi and lungs (which are parts of the respiratory system); the brain, spinal cord and nerves (which are parts of the nervous system); the heart, blood vessels and blood (which are parts of the cardiovascular system); the mouth, esophagus, stomach, intestines (bowels), liver, pancreas and gallbladder (which are parts of the digestive (gastrointestinal) system); the lymph vessels, lymph fluid, lymph nodes, tonsils, thymus and spleen (which are parts of the lymphatic system); the bones, cartilage, muscles and tendons (which are parts of the musculoskeletal system); and the skin, hair, nails and sweat glands (which are parts of the integumentary system).

As used in the present disclosure, the term "anatomical region" refers to an area of the body. Examples of anatomical regions includes the thorax, abdomen, neck, head and pelvis. Other examples of anatomical regions includes: the cranial region; the facial region; the frontal region; the orbital or ocular region; the buccal region; the auricle or otic region; the nasal region; the oral region; the mental region; the cervical region; the thoracic region; the mammary region; the sternal region; the abdominal region; the umbilicus; the coxal region; the pubic region; the inguinal or groin region; the pubic region; the femoral region; the patellar region; the crural region; the fibular region; the tarsal region; the pedal region; the digital/phalangeal region; the hallux; the axillary region; the brachial region; the antecubital region; the antebrachial region; the carpal region; the palmar region; the digital/phalangeal region; the pollex; the scapular region; the dorsal region; the lumbar region; the sacral region; the acromial region; the brachial region; the olecranal region; the antebrachial region; the manual or manus region; the gluteal region; the femoral region; the popliteal region; the sural region; the calcaneal region; the plantar region; the trunk region; the cephalic region; the upper limb region; and the lower limb region.

The definitions and embodiments described in particular sections are intended to be applicable to other embodiments herein described for which they are suitable as would be understood by a person skilled in the art.

Detailed embodiments of the present disclosure are provided herein; however, it is to be understood that the disclosed embodiments are merely examples that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Referring to FIG. 1, there is shown a radiation dosimeter 100 for measuring radiation dose within a 2D or 3D region. The radiation dosimeter can allow real-time measurements of a radiation dose when irradiated by a radiation source. The measurements can be integrated over time. The radiation dosimeter 100 includes a phantom 102 and a radio-luminescent element 104. For example, deformation can happen to the phantom and/or the radio-luminescent element. The radiation source can be provided to irradiate the radiation dosimeter including the phantom and the radio-luminescent element(s). The radiation source may provide any type of radiation known for radiotherapy, for example, X-rays, electron beams, proton sources, or others.

The phantom can be deformable. The phantom can be formed of a deformable material. The radio-luminescent element can also be deformable. Further, when there is a grid of radio-luminescent elements, one or more of them can be deformable. In alternative, the radio-luminescent elements of the grid are deformable. In that case, when the phantom is deformed, the radio-luminescent elements are not deformed but are displaced (i.e. changes position) within the phantom as a result of the phantom's deformation.

There can be a plurality of deformation scenarios. In one embodiment, the phantom is not being deformed while the radio-luminescent element(s) are being deformed. In another embodiment, the phantom is being deformed while the radio-luminescent element(s) are being not deformed. In a further embodiment, both the phantom and scintillators are being deformed.

The phantom can be composed of liquid or solid materials (plastics, gels). These can be water or tissue-equivalent. The phantom can be transparent but can include opaque markers. The deformable material can be a heterogeneous and/or porous material. For example, the heterogeneous material can be a natural sponge or a synthetic sponge. The phantom can also include a tissue-equivalent tumor.

The phantom can represent any suitable organ or body part, such as a lung or prostate. The phantom can also represent an organ (such as a lung, liver, heart, etc.) or an anatomical region (such as the abdomen, a thorax, a neck, a head, and a pelvis).

The phantom can have any suitable shape, including the shape of the organ or body region that it is representing. The phantom can also have a uniform shape or cross-section, such as rectangular (as shown in FIG. 1), cubic, cylindrical, egg-shaped, oval, or others. For example, the phantom's dimension could range from 1 cm$^3$ up to the size of a human body.

Referring back to FIG. 1, the radio-luminescent element 104 is located within the phantom. The radio-luminescent element 104 can be configured to generate optical energy in response to irradiation. The radio-luminescent element 104 can be a plastic radio-luminescent element. The radio-luminescent element can be deformable. During irradiation, light is generated by the radio-luminescent element 104 in an amount proportional to the radiation dose that strikes the active area of the radio-luminescent element 104. For example, the radio-luminescent element's dimension could range from 0.5 $mm^3$ to 25 $mm^3$. For example, the radio-luminescent element's dimension could range from 0.1 $cm^3$ up to the size of a human body.

The radio-luminescent element can include a scintillator, such as an organic scintillator. The organic scintillator can be a liquid. The radio-luminescent element can also include a plastic scintillator. For example, the scintillator can be of the BC-418 type. As an alternative, the scintillator can be an organic scintillator based, for example, on pure or diluted oxazoles or oxadiazoles in a transparent matrix, an organic scintillator obtained by chemical synthesis onto which have been grafted oxazole or oxadiazole chromophores of microscopic or nanometric size.

The radio-luminescent element can also include an inorganic scintillator (i.e. crystals such as NaI, BGO, etc.). For example, the scintillator can be produced in an inorganic scintillating material, such as sodium iodide (NaI), cadmium telluride (CdTe), titanium monoxide (TiO), and yttrium aluminium garnet doped with cerium (YaG). The inorganic scintillator material can be a rare earth or other metal halide; a rare earth sulfide, oxysulfide, germinate, silicate, or aluminum garnet; $CdWO_4$; $CaWO_4$; ZnS; ZnO; ZnCdS, another suitable scintillator material, or the like.

The radio-luminescent element can also include quantum dots; cerenkov emitting materials (e.g. water); and/or fluorescence emitting materials.

Figure 2:
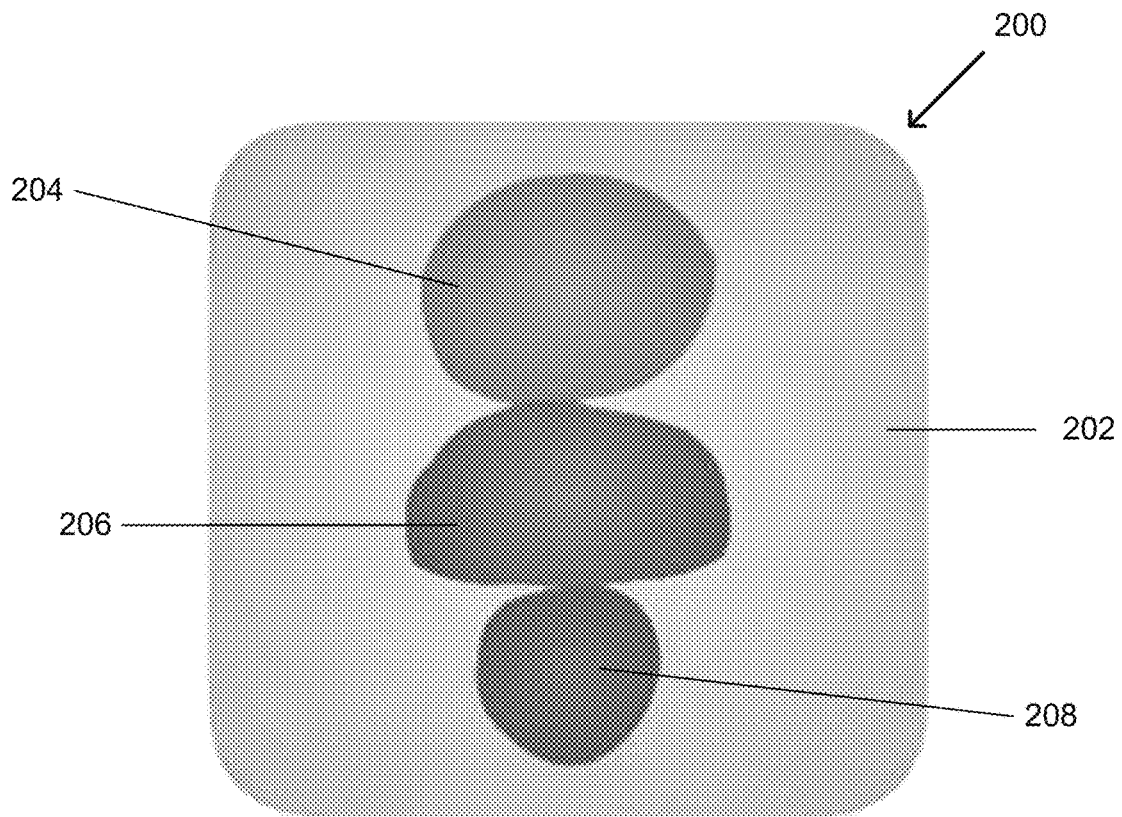
FIG. 2 shows a radiation dosimeter according to one example.

Referring to FIG. 2, there is shown a radiation dosimeter 200 for measuring radiation dose within a 2D or 3D region. The radiation dosimeter 200 includes a phantom 202 and radio-luminescent elements 204, 206, 208. The radio-luminescent elements can be deformable. They are located within the phantom for detecting the radiation dose at multiple points in the 2D or 3D region that is irradiated. For example, the radio-luminescent elements can be contiguous.

The radio-luminescent elements can have different light emission spectra. While three radio-luminescent elements are shown, this is for illustrative purposes only and one skilled in the art will understand that a different number of radio-luminescent elements may be used. During operation, in response to irradiation, light is generated by the radio-luminescent elements in an amount proportional to the radiation dose that strikes the active area of the radio-luminescent elements.

Figure 3:
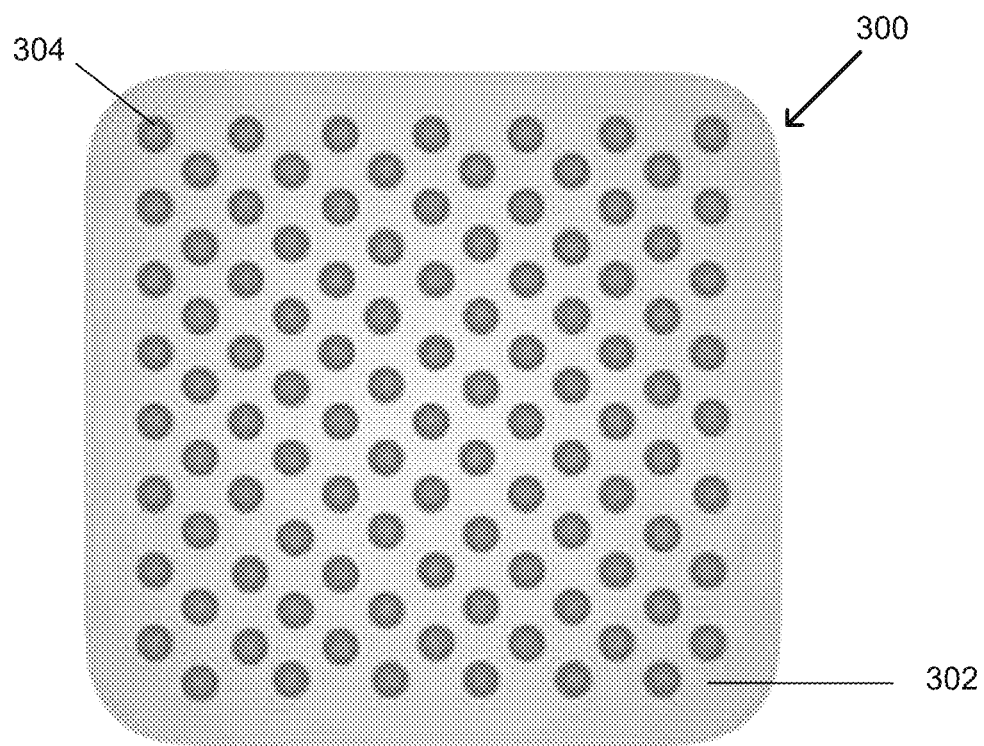
FIG. 3 shows a radiation dosimeter according to one example.

Referring to FIG. 3, there is shown a radiation dosimeter 300 for measuring radiation dose within a 2D or 3D region. The radiation dosimeter 300 includes a phantom 302 and radio-luminescent elements 304. The radio-luminescent elements 304 have the same optical emission spectrum. The radio-luminescent element 304 can be placed at regular intervals throughout the phantom to form a 2D or 3D grid for measuring radiation within an irradiated 2D or 3D region. There can be a plurality of deformation scenarios as explained previously. For example, the phantom is being deformed while the radio-luminescent element(s) are not being deformed. The radio-luminescent elements can be displaced as a result of the phantom's deformation, but their shape does not change.

Figure 4:
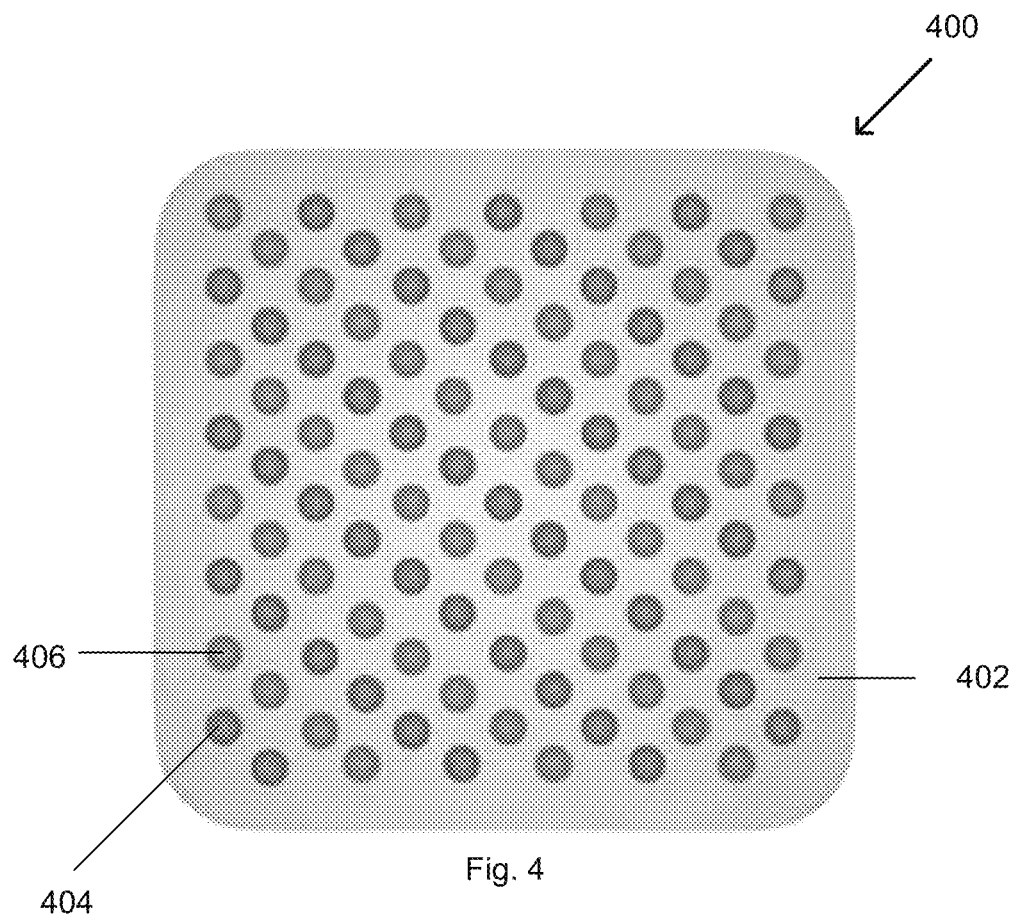
FIG. 4 shows a radiation dosimeter according to one example.

Referring to FIG. 4, there is shown a radiation dosimeter 400, which includes a phantom 402 and radio-luminescent elements 404 and 406. The radio-luminescent elements 404 and 406 have different optical emission spectra. The radio-luminescent elements 404 and 406 can be placed at regular intervals throughout the phantom to form a 2D or 3D grid for measuring radiation within an irradiated 2D or 3D region. There can be a plurality of deformation scenarios as explained previously. For example, the shape of the phantom can be deformed while the shape of the radio-luminescent element(s) does not change. However, the radio-luminescent elements can be displaced within the phantom because of the phantom's deformation.

In one embodiment, the radio-luminescent elements 304, 404 and 406 include a diameter of about 0.5 to 1 mm and a length of about 1-5 mm. In another embodiment, the radio-luminescent element's dimension can range from 0.5 $mm^3$ to 25 $mm^3$. Further, the radio-luminescent elements can be shaped in any suitable dimensions. The radio-luminescent elements can include water-equivalent materials. Some example materials that can be used for the radio-luminescent elements include, but are not limited to, organic (plastic) materials such as polystyrene and polyvinyltoluene as well as inorganic materials such as, but not limited to, Sodium Iodide (NaI), Bismuth Germanate (BGO), Caesium Iodide (CsI), Calcium Fluoride (CaF2), Aluminum Oxide (Al2O3) and the like.

Figure 5:
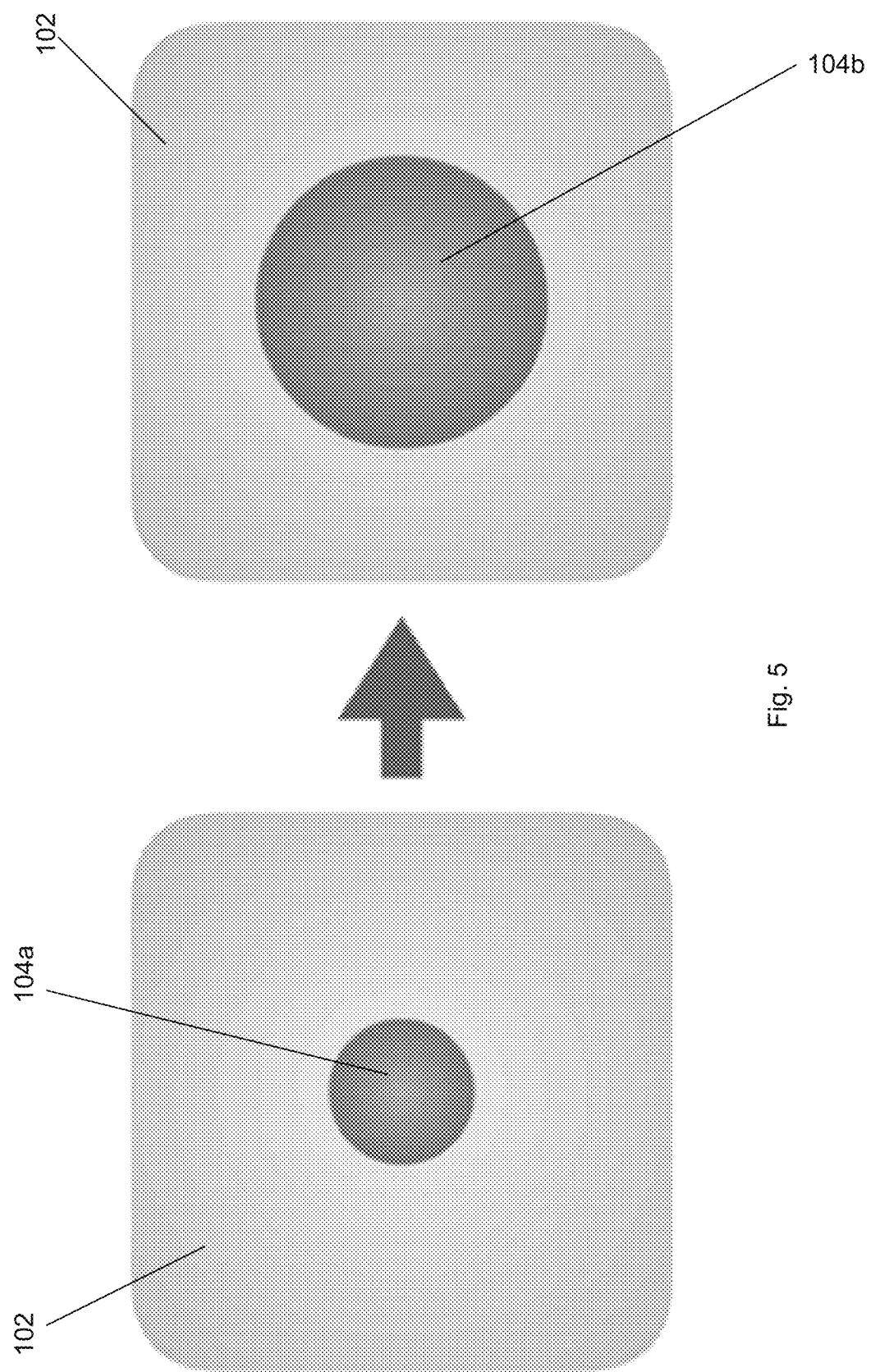
FIG. 5 shows deformation of the radio-luminescent element of FIG. 1 according to one example.

Referring to FIG. 5, there is shown the deformation of the radio-luminescent element 104 in FIG. 1. The radio-luminescent element 104 is deformed from 104a to 104b. An actuator (not shown) can be configured to deform the deformable radio-luminescent element 104. In one embodiment, possible deformations include volume changes, which can be performed with a system of pumps. Further, deformations modifying shapes can be performed with mechanical pressures, actuators and/or motors. These deformation tools can be located outside the phantom.

Figure 6:
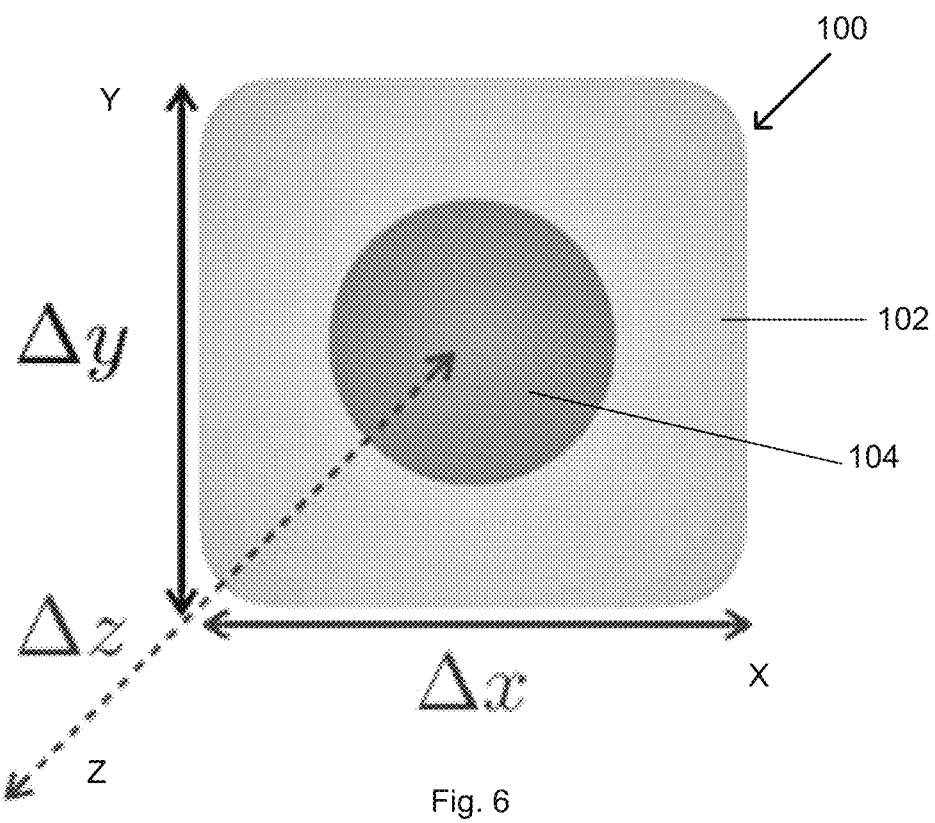
FIG. 6 is shows deformation imposed to the radio-luminescent element of FIG. 1 according to one example.

Referring to FIG. 6, there is shown an exemplary embodiment of the deformation imposed to the radio-luminescent element of FIG. 1. The deformation of the radio-luminescent element 104 can be measured in a 3D space in reference to the x, y and z axes. For example, Δx can represent the deformation of the radio-luminescent element along the X axis; Δy can represent the deformation of the radio-luminescent element along the Y axis; and Δz can represent the deformation of the radio-luminescent element along the Z axis.

Figure 7:
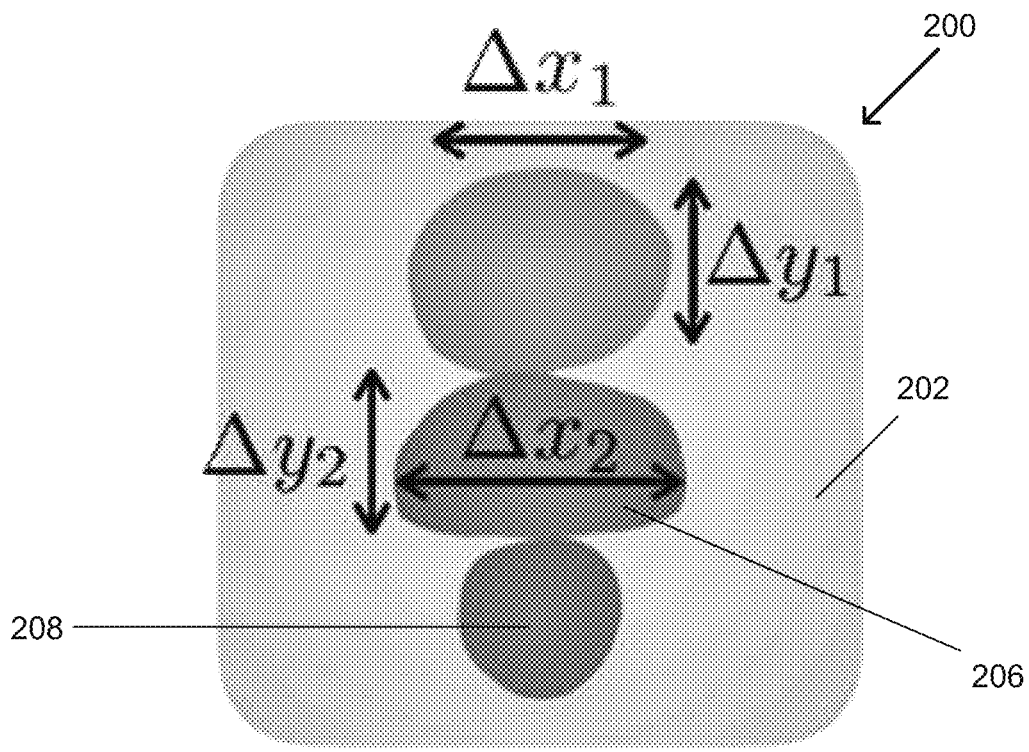
FIG. 7 shows deformations imposed to radio-luminescent elements of FIG. 2 according to one example.

Referring to FIG. 7, there are shown the deformations imposed to radio-luminescent elements 204, 206 and 208 of FIG. 2. The radio-luminescent element 204 is deformed by (Δx1, Δy1) along the X and Y axes. The radio-luminescent element 206 is deformed by (Δx2, Δy2) along the X and Y axes. The radio-luminescent element 208 is not deformed.

A system of pumps can be used to change the volume of the radio-luminescent element(s). The shape of the radio-luminescent element(s) can be deformed with a mechanical pressure, an actuator and/or a motor. These deformation tools can be located outside the phantom. The radio-luminescent element(s) and the phantom can be deformed by a different deformation system. In one embodiment, the phantom and/or the radio-luminescent elements can be configured to take a shape of an anatomical region. For example, the phantom can be deformed to take the shape of an organ or a region of the body, such as the abdomen, a thorax, a neck, a head, and a pelvis. For example, the radio-luminescent elements can be deformed to take the shape of an organ or body part, such as a lung, prostate, liver or heart.

Figure 8:
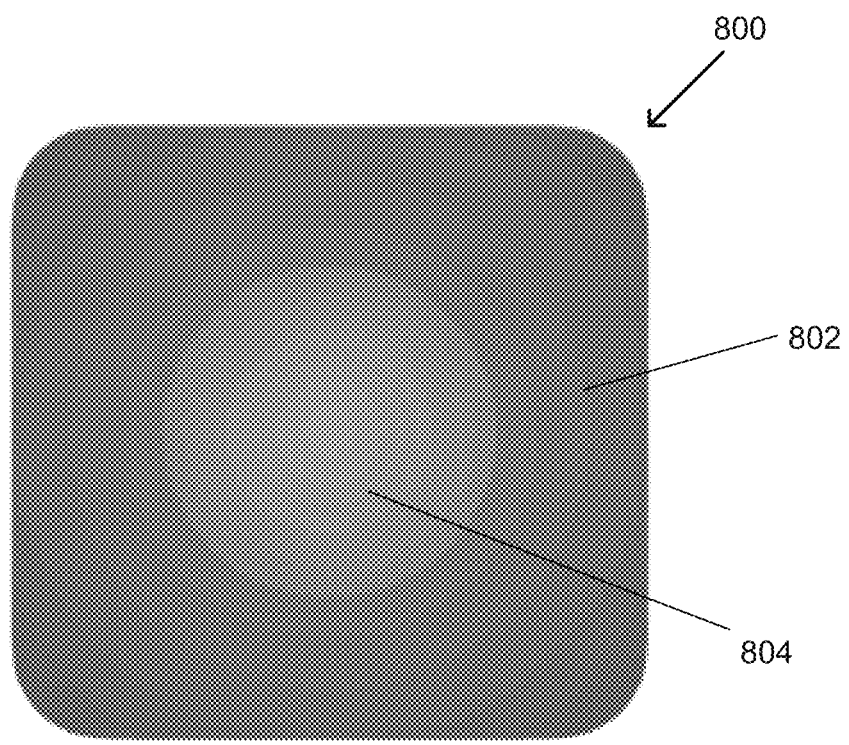
FIG. 8 shows a radiation dosimeter according to one example.

Referring to FIG. 8, there is shown a radiation dosimeter 800 for measuring radiation dose within a 2D or 3D region. The radiation dosimeter 800 includes a structure 802 and a radio-luminescent element 804. For example, the structure and the radio-luminescent element can be deformed. The radiation dosimeter can allow real-time measurements of a radiation dose when irradiated by a radiation source. The radiation source can be provided to irradiate the radiation dosimeter including the structure and the radio-luminescent element(s). The radiation source may provide any type of radiation known for radiotherapy, for example, X-rays, electron beams, proton sources, or others.

Referring back to FIG. 8, the radio-luminescent element 804 is located within the structure 802. The radio-luminescent element 804 is configured to generate optical energy in response to irradiation.

The structure 802 includes a scintillating material. The scintillating material emits light when exposed to radiation. The scintillating material can have a different spectrum than the radio-luminescent element 804. The scintillating material can act as the structure. An example would be a plastic scintillator submerged in a liquid scintillator. For that example, another phantom material would be needed to contain the liquid scintillator.

The structure 802 can be deformable. Possible deformations of the structure include volume changes, which can be performed with a system of pumps. Further, deformations modifying shapes of the structure can be performed with mechanical pressures, actuators and/or motors. These deformation tools can be located outside the structure.

Further, a system of pumps can be used to change the volume of the radio-luminescent element(s). The shape of the radio-luminescent element(s) can be deformed with a mechanical pressure, an actuator and/or a motor. These deformation tools can be located outside the phantom.

Figure 9:
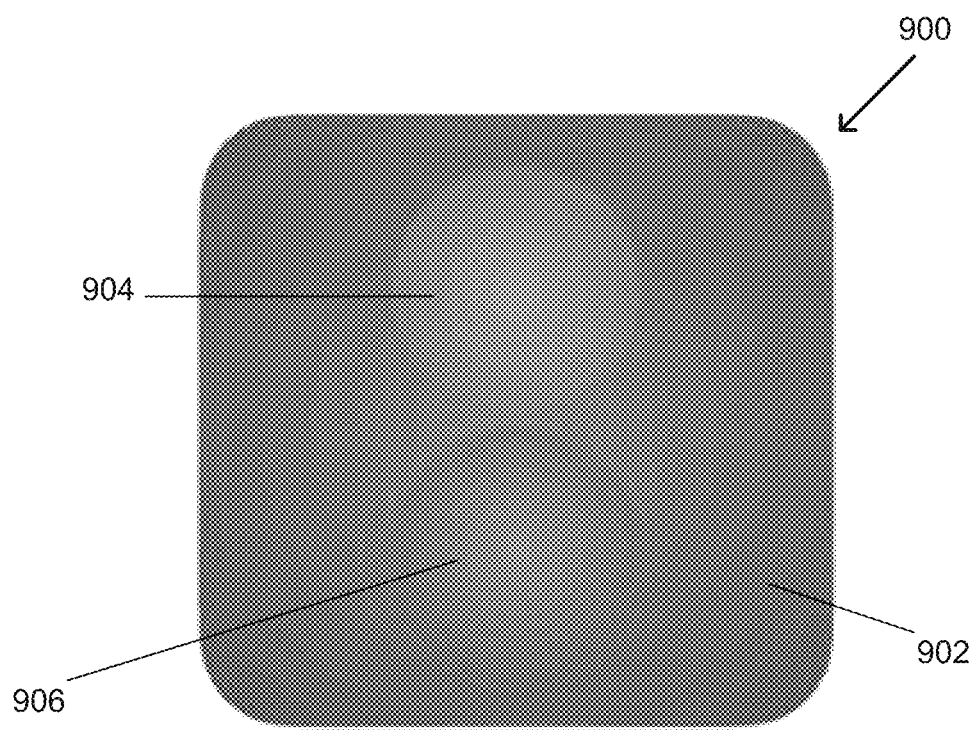
FIG. 9 shows a radiation dosimeter according to one example.

Referring to FIG. 9, there is shown a radiation dosimeter 900 for measuring radiation dose within a 2D or 3D region. The radiation dosimeter 900 includes a structure 902 and radio-luminescent elements 904 and 906. The radio-luminescent elements 904 and 906 can be deformable. They are located within the structure 902 for detecting the radiation dose at multiple points in the 2D or 3D region that is irradiated. For example, the radio-luminescent elements can be contiguous. The structure 902 includes a scintillating material that emits light when exposed to radiation. The scintillating material can have a different spectrum than the radio-luminescent elements 904 and 906. The structure 902 can be deformable.

Figure 10:
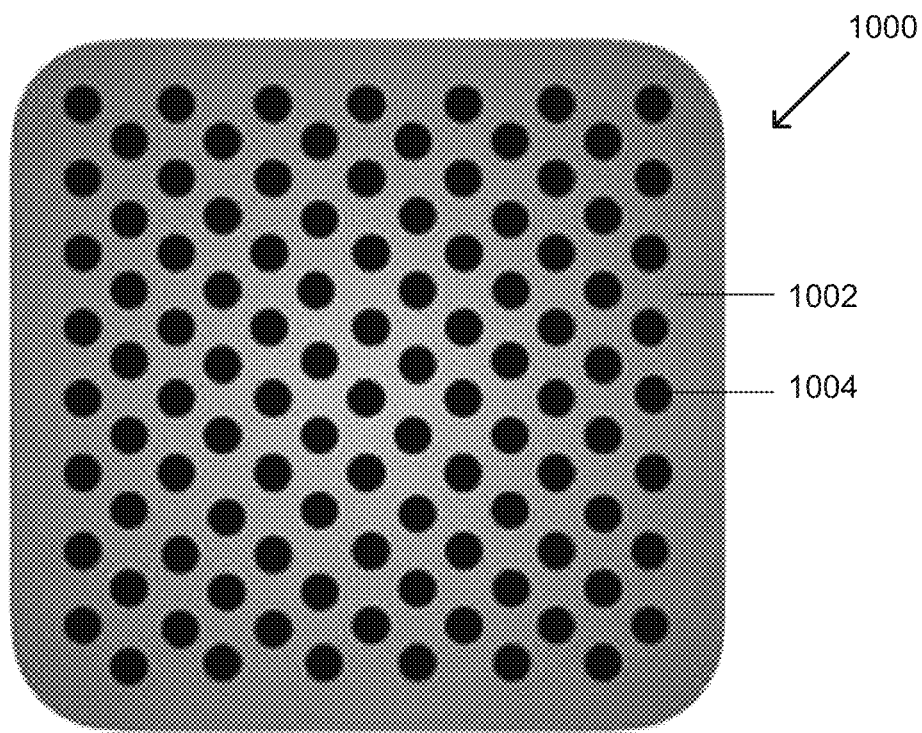
FIG. 10 shows a radiation dosimeter according to one example.

Referring to FIG. 10, there is shown a radiation dosimeter 1000 for measuring radiation dose within a 2D or 3D region. The radiation dosimeter 1000 includes a structure 1002 and a plurality of markers 1004. The structure 1002 includes a scintillating material. The markers can be placed at regular intervals throughout the structure. The markers can be opaque. The markers can be used to measure the vector field of the deformation.

Figure 11:
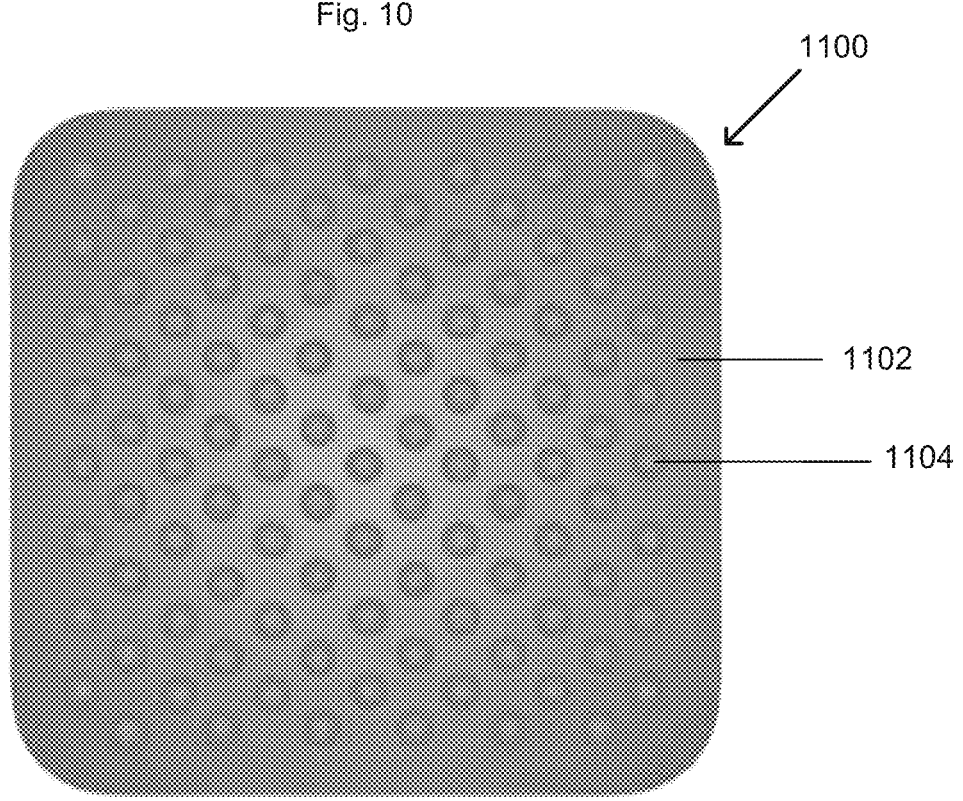
FIG. 11 shows a radiation dosimeter according to one example.

Referring to FIG. 11, there is shown a radiation dosimeter 1100, which includes a structure 1102 and radio-luminescent elements 1104. The radio-luminescent elements 1104 can have the same optical emission spectrum. The radio-luminescent elements 1104 can be placed at regular intervals throughout the structure 1102 to form a 2D or 3D grid for measuring radiation within an irradiated 2D or 3D region. There can a plurality of deformation scenarios as explained previously. For example, the structure is deformed while the radio-luminescent element(s) are not deformed. Further, the radio-luminescent elements can be displaced and/or rotated as a result of the phantom's deformation, but not deformed.

The radio-luminescent elements 1104 can be contiguous. The radio-luminescent elements can include water-equivalent materials. The radio-luminescent elements 1104 can be deformable.

The structure 1102 includes a scintillating material that emits light when exposed to radiation. The scintillating material can have a different spectrum than the radio-luminescent element 1104. The structure 1102 can be deformable.

Figure 12:
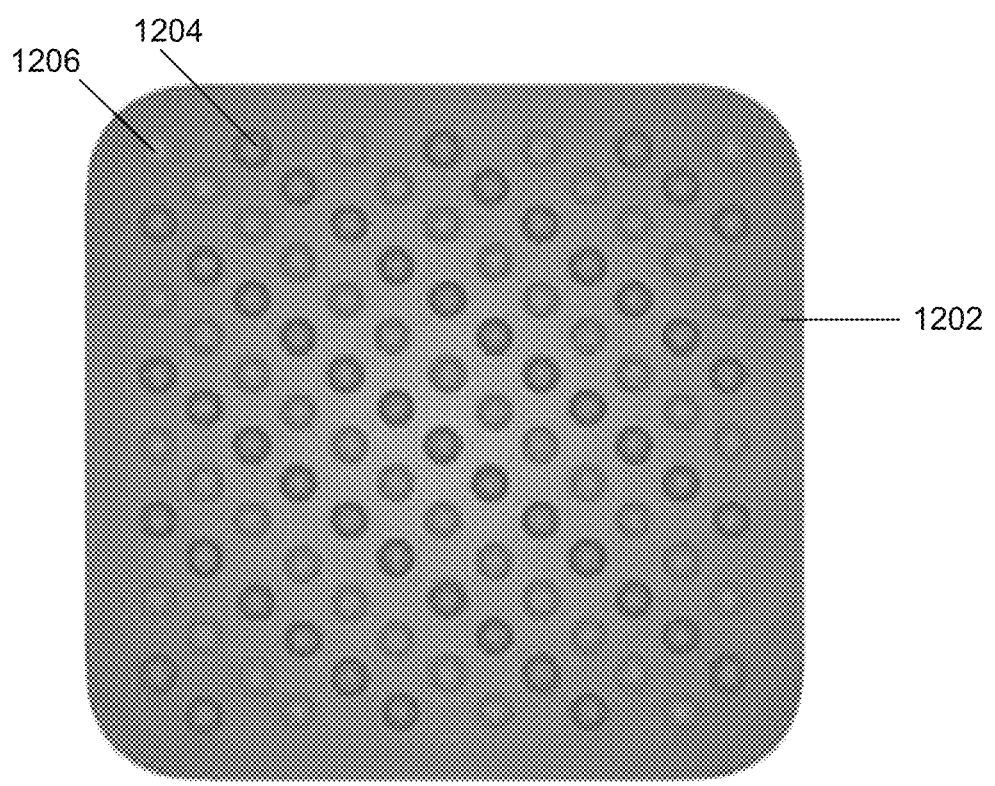
FIG. 12 shows a radiation dosimeter according to one example.

Referring to FIG. 12, there is shown a radiation dosimeter 1200, which includes a structure 1202 and radio-luminescent elements 1204 and 1206. The structure 1202 includes a scintillating material. The radio-luminescent elements radio-luminescent elements 1204 and 1206 can have different optical emission spectra. The radio-luminescent elements 1204 and 1206 can be placed at regular intervals throughout the structure 1202 to form a 2D or 3D grid for measuring radiation within an irradiated 2D or 3D region. The structure 1202 and the radio-luminescent elements 1204 and 1206 can be deformable. There can be a plurality of deformation scenarios as explained previously. For example, the structure is deformed while the radio-luminescent element(s) are not deformed. However, the radio-luminescent elements can be displaced and/or rotated as a result of the phantom's deformation, but their shape does not change.

In one embodiment, the structure and/or the radio-luminescent elements can be configured to take a shape of anatomical regions. For example, the structure can be deformed to take the shape of an organ (such as a lung, liver, heart, etc.) or a region of the body (such as the abdomen, a thorax, a neck, a head, and a pelvis). For example, the radio-luminescent elements can be deformed to take the shape of an organ or body part, such as a lung, prostate, liver or heart. Further, a non-exhaustive list of organ or body part could also include rectum, mandibles, trachea, bladder, etc.

A radiation system for measuring radiation dose within a 2D or 3D region is provided herein. The radiation system includes a phantom and a plurality of deformable radio-luminescent elements located within the phantom and configured to generate optical energy in response to irradiation at multiple points in the 2D or 3D region. Embodiments of the phantom and radio-luminescent elements are illustrated in FIGS. 1 to 7. The deformable radio-luminescent elements can have different optical emission spectra. A first actuator can be configured to deform at least one of the deformable radio-luminescent elements.

The phantom can include a deformable material. The system can include a second actuator is configured to deform the phantom. The first and second actuator can be the same. Examples of actuators are a motor-driven rod or piston or a bladder with pressurized fluid. A radiation source is provided to irradiate the phantom and the radio-luminescent elements. The radiation source may provide any type of radiation known for radiotherapy, for example, X-rays, electron beams, proton sources, or others.

A video camera and/or scanner can be configured to acquire radiation data in the form of lights emitted by the radio-luminescent elements. For example, radiation data can be acquired using a photodetectors such as spectrometer or video camera (CCD, CMOS, plenoptic).

For example, multiple photodetectors (e.g. multiple cameras, etc.) can be used to acquire radiation data (e.g. images, etc.) of the dosimeter from different points of view. They can be positioned to image perpendicular planes (XY vs XZ vs YZ) or be positioned such that they form stereoscopic pairs.

The radiation data can be acquired in real-time. Once acquired the radiation data is sent to a processor for processing. The processor (e.g., computer or computing devices) can be used to process the acquired radiation data. The radiation data may be generated and/or recorded while the phantom and/or the radio-luminescent elements is being deformed and/or irradiated.

The radiation data can be recorded while one or more of the deformable radio-luminescent elements are being deformed and/or irradiated. The radiation data can be recorded from different angles. The radiation data can allow a tomographic reconstruction of the radiation dose for each voxel of the irradiated 3D region (or volume).

In another embodiment, a radiation system includes a structure having a scintillating material and a plurality of deformable radio-luminescent elements located within the structure and configured to generate optical energy in response to irradiation at multiple points in the irradiated 2D or 3D region. Embodiments of the structure and radio-luminescent elements are illustrated in FIGS. 8 to 12. The deformable radio-luminescent elements can have different optical emission spectra. A first actuator can be configured to deform at least one of the deformable radio-luminescent elements.

The scintillating material of the structure can be deformed by a second actuator. The first and second actuator can be the same. Radiation data can be recorded while the scintillating material of the structure and/or the deformable radio-luminescent elements is/are being deformed and/or irradiated. The radiation data can be recorded from different angles. The radiation data can allow a tomographic reconstruction of the radiation dose for each voxel of the 3D region.

Measuring radiation dose in a dosimeter within a 2D or 3D region can be performed in real-time such that dose is measured as the radiation is being delivered to the dosimeter. The dosimeter can be deformed while being irradiated. Thus, the deformation of the phantom can occur as the radiation is being delivered to the phantom of the dosimeter and as the radiation dose is being measured. Further, the deformation of the radio-luminescent elements can occur as the radiation is being delivered to the radio-luminescent elements and as the radiation dose is being measured.

The radiation can be constant. To irradiate the dosimeter, the radiation source can be one of those frequently encountered in medical treatments. For example, these include continuous and pulsed sources. The radiation can be pulsed (every few milliseconds). For example, to simulate a plurality of treatment scenarios, the energy density per pulse can be between 0.1 and 10 Joules per square centimeter of treatment area. These pulses can be repeated at a rate of between 0.1 and 5000 Hertz. For example, there can be a pulse every 2 ms (2000 Hz). The number of pulses can range between 1 and 1000 pulses. For example, the radiation can be applied to a treatment area ranging from 0.8 cm$^2$ to 1600 cm$^2$. For example, the radiation can be applied to a treatment area ranging from 1600 cm$^2$ up to the size of a human body. For example, the radiation can be applied to a treatment volume ranging from 0.8 cm$^3$ to 1600 cm$^3$. For example, the radiation can be applied to a treatment volume ranging from 1600 cm$^3$ up to the size of a human body.

A method of measuring radiation dose in a dosimeter within a 2D or 3D region includes deforming a phantom or deforming one or more deformable radio-luminescent elements located within the phantom and configured to generate optical energy in response to irradiation. Embodiments of the phantom and radio-luminescent elements are illustrated in FIGS. 1 to 7. The method also includes irradiating the one or more deformable radio-luminescent elements using a radiation source and measuring the radiation dose in the deformable radio-luminescent elements.

The method can include measuring the radiation dose from different angles. The method can also include displaying a tomographic reconstruction of the radiation dose for each voxel of the 2D or 3D region. The deforming step can include deforming the phantom and/or the one or more deformable radio-luminescent elements to simulate a deformation of an organ or an anatomical region. The organ can be one of the organs as previously defined in paragraph 63. The anatomical region can be one of the anatomical regions as previously defined in paragraph 64.

The method can include deforming the radio-luminescent elements while the phantom is not deformed. The method can also include deforming the phantom while the radio-luminescent elements are not deformed. The method can further include deforming both the phantom and the one or more deformable radio-luminescent elements.

In another embodiment, a method of measuring radiation dose in a dosimeter within a 2D or 3D region includes deforming a structure having a scintillating material and deforming one or more deformable radio-luminescent elements located within the structure. Measuring radiation dose in the dosimeter can be performed in real-time such that dose is actively measured as the radiation is being delivered to the dosimeter. The dosimeter can be deformed while being irradiated. Thus, the deformation of the structure can occur as the radiation is being delivered to the structure of the dosimeter and as the radiation dose at the structure surface and/or volume is being measured. Further, the deformation of the radio-luminescent elements can occur as the radiation is being delivered to the radio-luminescent elements and as the radiation dose at the radio-luminescent elements is being measured.

Embodiments of the structure and radio-luminescent elements are illustrated in FIGS. 8 to 12. The method includes irradiating the structure or the radio-luminescent elements using a radiation source; and measuring the radiation dose in the structure or the deformable radio-luminescent elements.

The method can include measuring the radiation dose from different angles. The method can also include displaying a tomographic reconstruction of the radiation dose for each voxel of the 2D or 3D region.

The deforming step can include deforming the structure to simulate a deformation of an organ or an anatomical region. The deforming step can include deforming one or more deformable radio-luminescent elements to simulate a deformation of an organ or an anatomical region. The organ can be one of the organs as previously defined in paragraph 63. The anatomical region can be one of the anatomical regions as previously defined in paragraph 64.

The method can include deforming the deformable radio-luminescent elements while the structure is not being deformed. The method can also include deforming the structure while the radio-luminescent elements are not deformed. The method can further include deforming both the structure and the one or more deformable radio-luminescent elements.

Example #1

Figure 13:
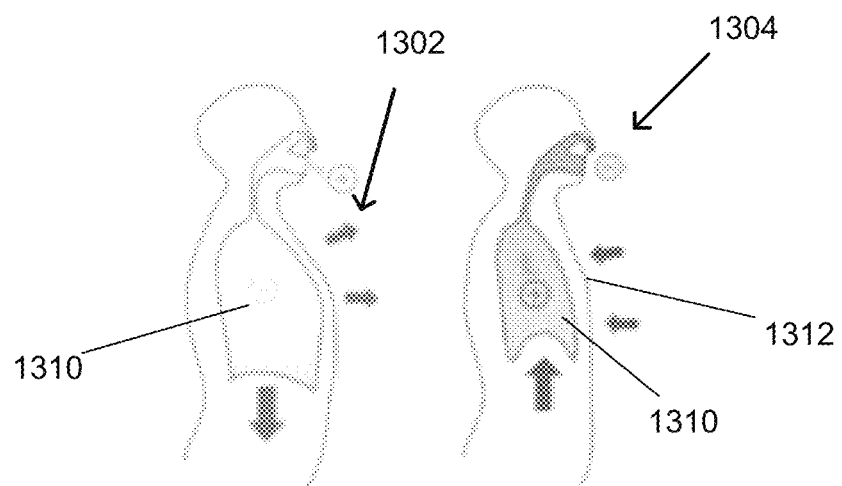
FIG. 13 shows an example of expansion and compression of the thorax region.

FIG. 13 shows an example of expansion 1302 and compression 1304 of the thorax 1312 and lung 1310 of a human body when breathing. During inhalation, the lung cavity expands. During exhalation, the chest tightens and the lung cavity compresses.

Figure 14:
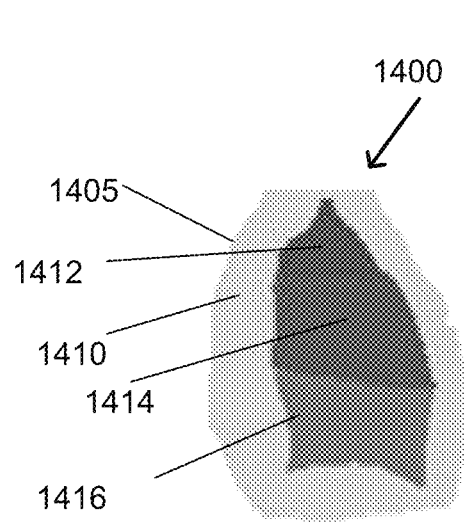
FIG. 14 shows a deformable dosimeter according to one example.
Figure 15:
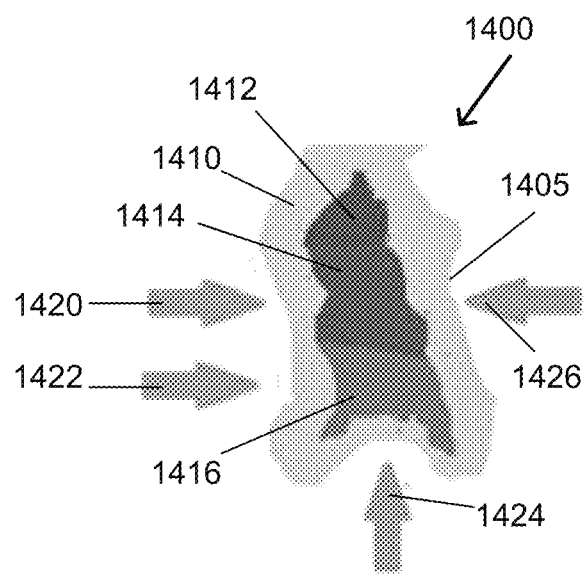
FIG. 15 shows deformations of the dosimeter of FIG. 14 according to a deformation scenario.

FIG. 14 shows a deformable dosimeter 1400 that takes the shape of the chest region for measuring radiation dose. FIG. 15 shows the deformable dosimeter 1400 of FIG. 14 being deformed by a system of actuators 1420, 1422, 1424 and 1426 that apply a force on the external surface 1405 of the radiation dosimeter. The radiation dosimeter 1400 includes a structure 1410 and radio-luminescent elements 1412, 1414 and 1416. The structure 1410 can be deformed by a system of actuators to take the thorax during exhalation. As the structure is being deformed, the radio-luminescent elements 1412, 1414 and 1416 can be deformed as well to take the shape of a lung cavity during exhalation. For example, the force exerted on the external surface of the structure is transferred to the radio-luminescent elements, As such, a radiation dose can be measured in real-time while the structure and the radio-luminescent elements are being irradiated and deformed. This allows gathering of multiple dose points in a target region of the dosimeter for 2D or 3D reconstruction of the radiation dose. This also allows the evaluation of effects of the irradiation on regions surrounding the target region. The dosimeter 1400 can permit simulation of various deformation scenarios of a lung cavity such as volume expansion and compression while a region of the lung cavity is being irradiated.

When irradiated, the radio-luminescent elements 1412, 1414 and 1416 emit lights proportional to the dose of radiation. A photodetector (such as a spectrometer, camera CCD, etc.) can capture and measure lights emitted by the radio-luminescent elements. Properties of the radio-luminescent elements include: instantaneous emission of light in real-time; physical property equivalent to water or a tissue; can play the role of detector and phantom. The radio-luminescent elements can also have excellent spatial resolution and high reproducibility and stability.

The various embodiments of radiation dosimeters described herein provide several advantages, some of which include: 1) enabling real-time measurements of a radiation dose; 2) obtaining multiple dose points for a 2D or 3D reconstruction of the radiation dose, 3) simulating radiation in a target region the body, while evaluating effect to surrounding regions, 4) measuring radiation dose in each voxel of a target region, and 5) simulating deformation scenarios in a target region the body, including volume expansion and compression and discontinuity while being subject to radiation.

Organic scintillation detectors have enabled high-resolution, water-equivalent and real-time 3D dosimetry, but have not been used in the context of deformable dosimetry. For example, over the course of radiotherapy treatments, the anatomy of a patient may be deformed and/or change volume. Hence, deformable image registration (DIR) algorithms are increasingly used in clinics to either map organ contours or dose distributions from one image set to another. However, in low contrast tissues, the high number of degrees of freedom of these algorithms can lead to inaccuracies in the computed deformation vector field (DVF). Using those DVFs can result in incorrect voxel pairing, leading to errors in dose accumulation. Thus, validation of DIR algorithms can be advantageous. Radiochromic gels have proven their capacity to measure dose under deformation but are limited to measuring the cumulative dose as they are integrating dosimeters. In the present subject matter, a dosimeter is therefore provided to overcome these issues. For example, the dosimeter can be deformable.

For example, the dosimeter can be a 3D deformable water-equivalent scintillation dosimeter that provides real-time measurements of both the dose and deformation vector field. The dosimeter can combine the qualities demonstrated of volumetric scintillation dosimeters to the advantage of a deformable prototype.

Therefore, a dosimeter that validates deformable image registration algorithms and understands the dosimetric impact of anatomical variations is described in the present subject matter. The dosimeter can measure dose and deformation vector fields. The dosimeter can be deformable. The dosimeter can simultaneously measure dose and deformation vector fields in real-time.

Figure 16:
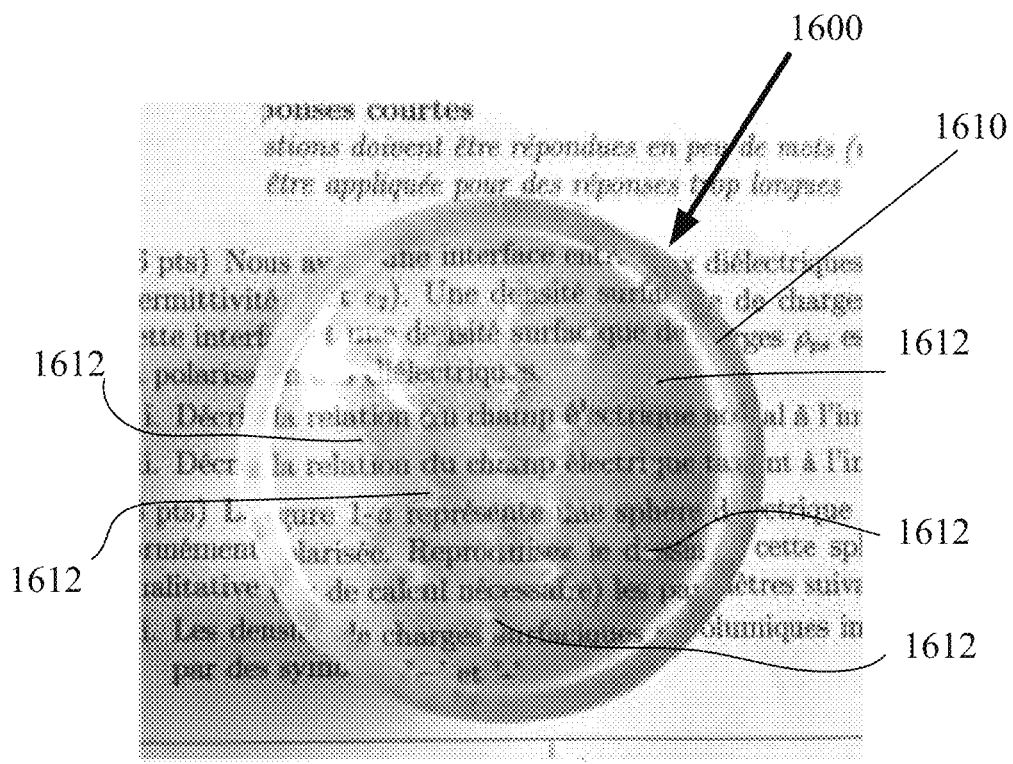
FIG. 16 shows a radiation dosimeter according to one example.

FIG. 16 shows an embodiment 1600 of such radiation dosimeter. The radiation dosimeter 1600 includes a structure (for example, a phantom) 1610 and radio-luminescent elements 1612. The dosimeter can be formable. The dosimeter can be transparent. The dosimeter can be made of rubber, such urethane rubber.

The structure can be clear. The structure can be flexible. For example, the structure can be a clear, flexible cylinder in which 19 scintillating fibers are embedded. For example, the radio-luminescent elements can be scintillating fibres. The structure 1610 can be deformed to take the shape of an organ or a region of the body such as the abdomen, a thorax, a neck, a head, and a pelvis. The structure 1610 can be deformed by an actuator. The radio-luminescent element 1612 can generate optical energy in response to irradiation. The radio-luminescent element 1612 can also be deformed.

For example, the cylinder can be made from an urethane liquid rubber compound (Smooth-On, Macongie, USA) cast in a silicone cylindrical mold (diameter: 6 cm, height: 1 cm). The compound can be degassed in vacuum prior to pouring to remove trapped air bubbles which would have reduced the final transparency of the resulting rubber. 19 BCF-60 scintillations fibers (Saint-Gobain Crystal, Hiram, Ohio, USA) (diameter: 1 mm, height: 1 cm) can be inserted in the cylindrical rubber guided by a specifically 3D-printed template.

The scintillating fibers can be embedded in the structure forming a 1×1×1 cm$^3$ triangular grid. The resulting detector's signal and composition can then be characterized. The density (g/cm$^3$) of the detector can be firstly extracted from a CT-scan (Siemens Somatom Definition AS Open 64, Siemens Healthcare, Forchheim, Germany), as well as that of blank urethane rubber cylinder (i.e. no fibers embedded) and a reference water volume. The pitch, current and energy of the scanner can be respectively set to 0.35, 60 mA and 120 kVp.

Figure 17:
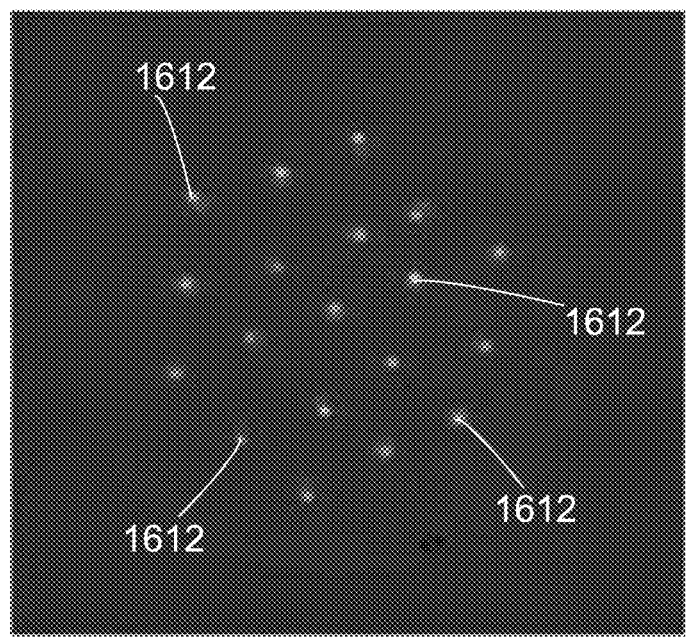
FIG. 17 shows an image of the radiation dosimeter of FIG. 16 during irradiation by a radiation source.

FIG. 17 shows a picture of the radiation dosimeter 1600 of FIG. 16 during irradiation by a radiation source. The picture is captured by a photodetector. As shown in FIG. 17, the radio-luminescent elements 1612 of the radiation dosimeter 1600 generate scintillation signals (i.e. optical energy) in response to the irradiation. In this specific embodiment, the radio-luminescent elements all have the same emission spectrum. In other embodiments, the radio-luminescent elements can have different emission spectra.

The structure 1610 (e.g. cylindrical matrix) can be radio-luminescent. For example, it can emit Cherenkov light. It can also emit scintillation as well.

For example, the detector can be irradiated with a 6 MV, 600 cGy/min photon beam (Clinac iX, Varian, Palo Alto, USA) while being imaged by a cooled polychromatic CCD camera Alta U2000 (Andor Technology, Belfast, United Kingdom). Background frames, i.e. images in absence of radiation, can be subtracted of the signal images and median temporal filter, over five acquisitions, additionally corrected the remaining transient noise.

The dose linearity, signal-to-noise ratio (SNR) and signal-to-background ratio (SBR) of the detector can be studied while varying the camera's integration time, the dose deposited or the dose rate. Signal-to-noise ratio describes a signal's detectability and is defined as the ratio of the mean pixel value to its standard deviation for each scintillation spot. Signal-to-background corresponds to the ratio of the signal to the standard deviation of the background.

Different dose rates can be achieved by varying the distance between the detector and the irradiation source to keep the integration time and delivered monitor units constant. Otherwise, the detector's center can be aligned with the isocenter of the linac. The developed dosimeter can be used to evaluate the dose variation and DVF resulting from a 1 cm compression.

Figure 18:
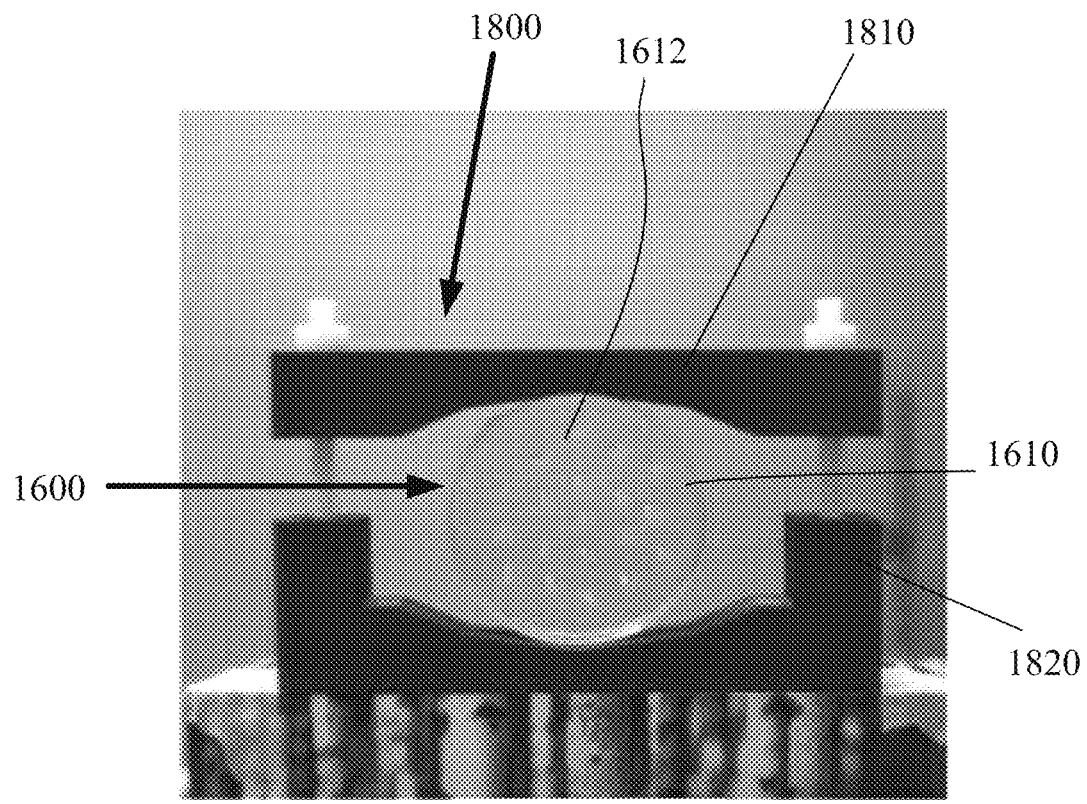
FIGS. 18 and 19 show a system for deforming a radiation dosimeter according to one example.

FIG. 18 shows a system 1800 for deforming a radiation dosimeter. The system 1800 includes a first plate 1810 and a second plate 1820. The first and second plate can be mounted relative to each other. The first and second plates can be slidably movable relative to each other. A radiation dosimeter can be positioned between the first and second plates. For example, the plates can be made of plastic.

Figure 19:
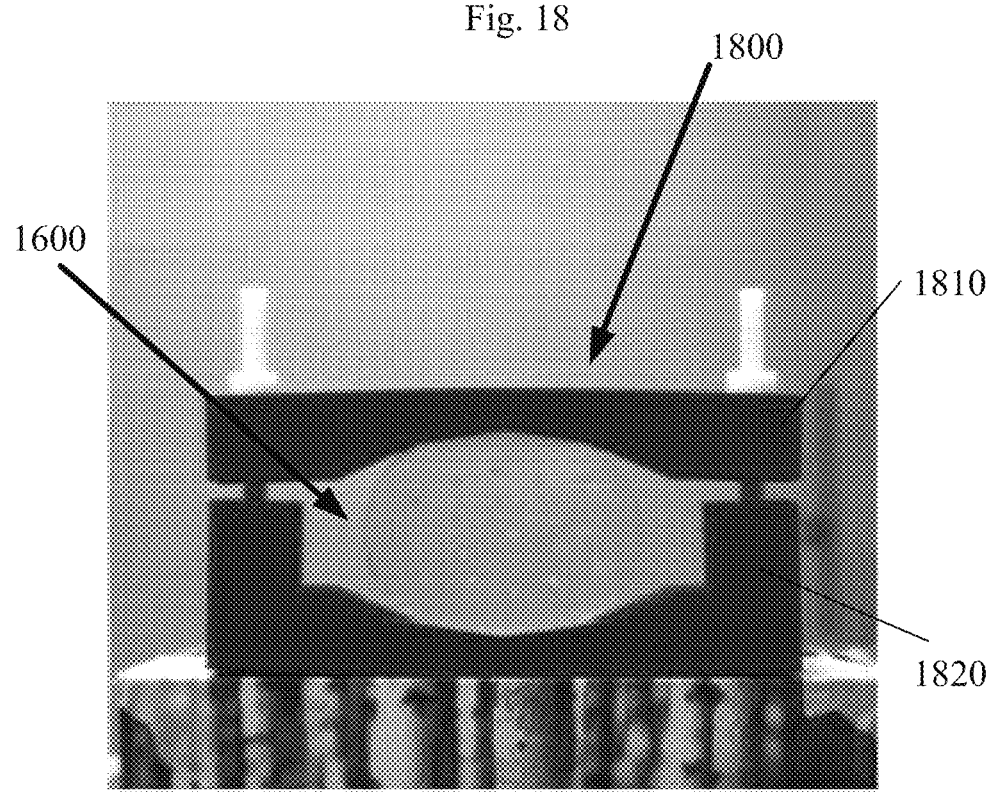

The dosimeter can be inserted between two plates distant by 6 cm (un-deformed) as shown in FIG. 18 and 5 cm (deformed) as shown in FIG. 19. The plates can be brought closer with two tighten nylon screws (FIG. 19). The dosimeter can be irradiated then CT-scanned, for both states. From the acquired CCD images, the dose and DVF can be extracted by tracking the centroid of each scintillating fiber.

The CT images can be further fed to a DIR algorithm and the computed DVF was extracted. The B-Spline algorithm from Plastimatch can be used to compute the DVF describing the transformation mapping the un-deformed dosimeter state to its deformed state. Mean square error (MSE) can be chosen to guide the cost function, with the regularization term set to 0.005. The resulting deformation vector field, obtained optically and from the DIR, can be then compared. Finally, analysis of the dose variation resulting from the deformation can be conducted using the scintillation light measured by the green pixels over each fiber's region of interest. The dose variation can also be calculated using the treatment planning system Pinnacle 9.2 (Philips Healthcare, Andover, Mass.) and compared to the one measured.

Evaluation of the voxels density values from CT-scans can yield (mean±standard deviation) densities of 1.002±0.005, 1.000±0.005 and 0.999±0.005 g/cm3 respectively for water, the urethane rubber and the urethane rubber containing the scintillating fibers array. The deformable detector's density presents no significant difference with water and thus can simultaneously act as a water-equivalent detector and phantom. Moreover, the scintillation fibers can be radio-transparent in relation to the urethane rubber, avoiding distortions of the dose deposition pattern.

Figure 20:
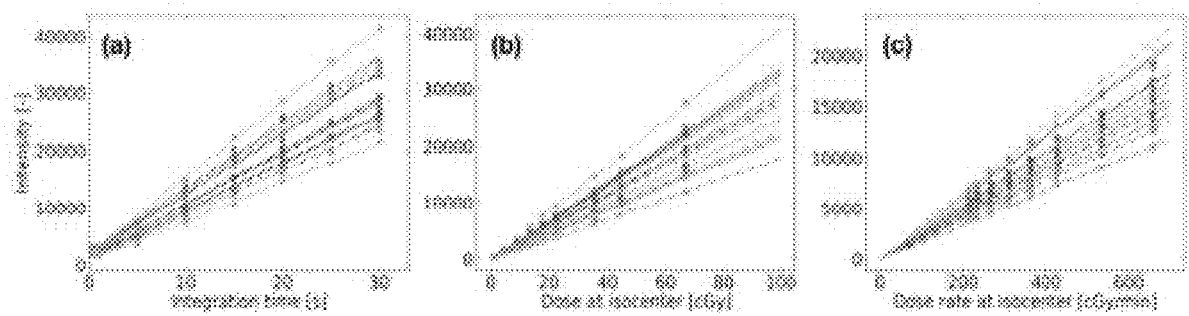
FIG. 20 shows the linearity of the scintillation signal as function of the integration time, dose deposited, and dose rate according to one example.

FIG. 20 shows the linearity of the scintillation signal as function of: (a) the integration time; (b) dose deposited at the isocenter; and (c) dose rate at the isocenter. $R^2$ can be lower than 0.99 for all cases.

For example, signal characterization of the detector can exhibit a linear dose-light relationship ($r^2$>0.999) for all of the 19 scintillation fibers (FIG. 20(b)). The signal to dose proportionality can remain linear ($r^2$>0.99) when varying the CCD's integration time from 0.1 to 30 s or the dose rate from 215 to 660 cGy/min (FIG. 20(a), FIG. 20(c)).

Figure 21:
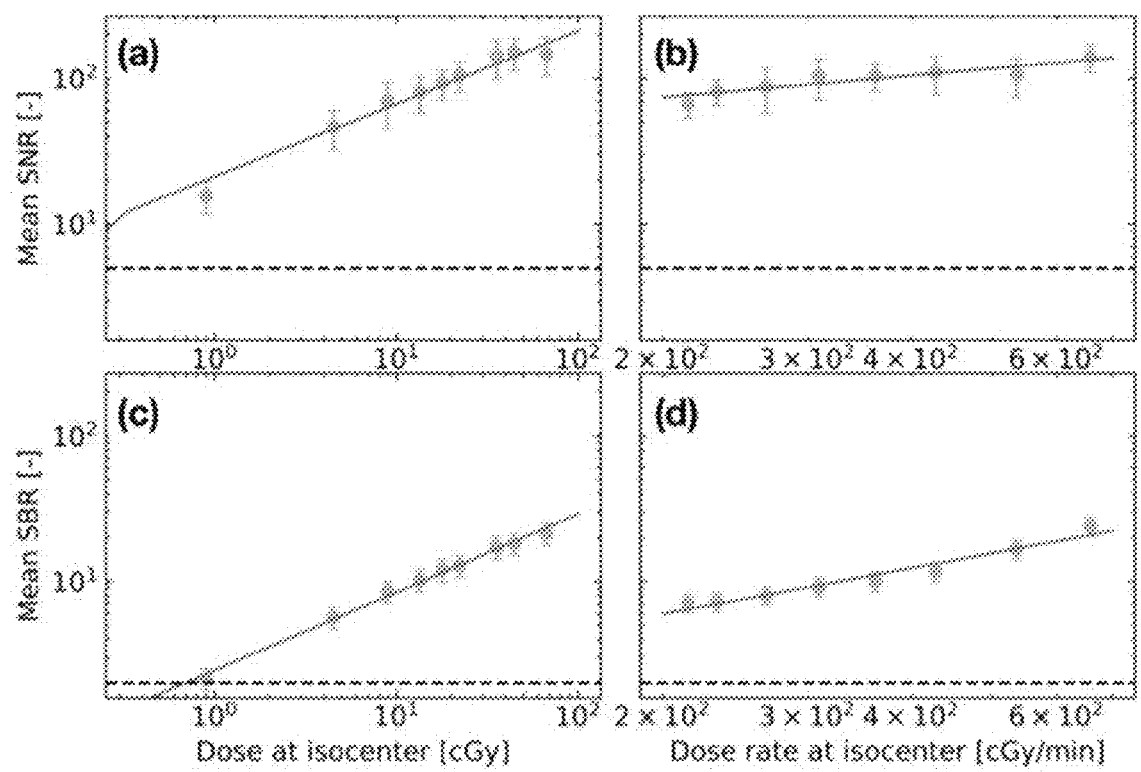
FIG. 21 shows Signal-to-noise ratio (SNR) and Signal-to-background ratio (SBR) as a function of the dose deposited and the dose rate according to one example.

FIG. 21 shows Signal-to-noise ratio (SNR) as a function of (a) the dose deposited and (b) the dose rate, and Signal-to-background ratio (SBR) as a function of (c) the dose deposited and (d) the dose rate at the isocenter. Dashed lines represent cut-off values for accurate detectability. Error-bars indicate the range of values obtained for the 19 scintillating fibres rather than the error on the measure.

For the SNR and SBR analysis, the signal remained over the detectability (SNR>5) and sensitivity (SBR>2) thresholds for all the explored doses and dose rates (FIG. 21). The performed study also suggests that a minimal dose of 1 cGy at the isocenter can be used to properly distinguish all of the scintillating fiber's signal from the background. However, those results can be obtained with an integration time of 10 s and hence could be improved by reducing the camera's integration time.

Figure 22:
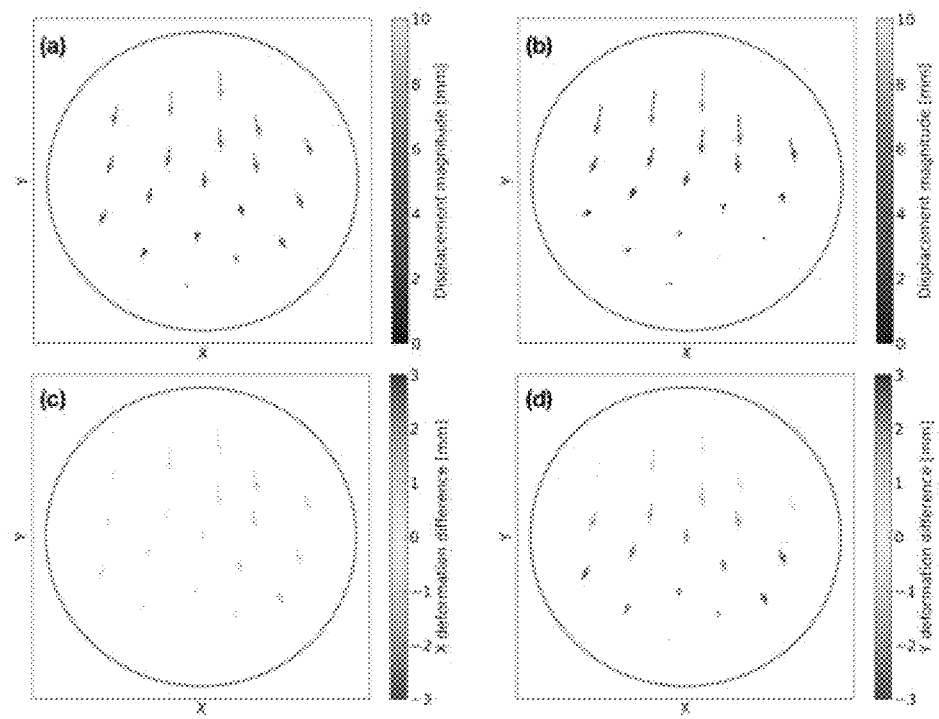
FIG. 22 shows deformation vector fields according to one example.

For example, each of FIGS. 22(a)-(d) show a deformation vector field measured with a deformable scintillation detector. The circle delimits the phantom's position in its un-deformed state. FIG. 22(a) represents the deformation vector field extracted from an array of 19 scintillating fibers embedded in a transparent, deformable and cylindrical phantom. The displacement vectors result from a 1-cm compression of the phantom. FIG. 22(b) presents the computed deformation vector field for the corresponding geometry with a deformable image registration algorithm. FIGS. 22(c) and (d) show the comparison between the measured and computed deformation vector fields.

The DVF computed presents the same shape, and order of magnitude as the one obtained optically. However, the DVF obtained numerically underestimated the horizontal deformation magnitude up to 1.2 mm (FIG. 22(c)) while overestimating the vertical deformation magnitude up to 2.9 mm (FIG. 22(d)). Overall, the applied compression resulted in a vertical downward shift and a horizontal shift towards the edges of the dosimeter. The largest vertical deformation can be obtained at the top of the dosimeter with measured and computed displacement of 8.0±0.02 and 7.8±0.02 mm. The scintillators near the right and left edges of the dosimeter presented the largest horizontal displacements, reaching 2.1±0.02 and 1.7±0.02 mm. These compare to predicted displacement of 1.5±0.02 and 1.4±0.02 mm. For example, since the compression is applied along the axial axis, the coronal axis deformation can be neglected.

Figure 23:
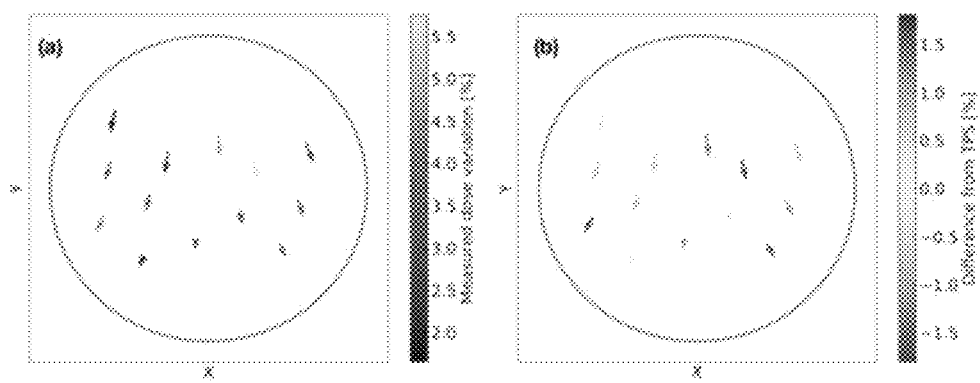
FIG. 23 shows dose variation resulting from the deformation of the dosimeter according to one example.

For example, FIGS. 23(a)-(b) present a measure of the dose variation that could be induced by the phantom's deformation. The dose variation is measured with an array of 19 scintillating fibers embedded in a transparent, deformable and cylindrical phantom at FIG. 23(a). Differences between the dose variation measured and the one computed with the treatment planning system is shown at FIG. 23(b). The circle delimits the phantom's position in its un-deformed state.

The variation is reported for 13 out of the 19 scintillating fibers. The remaining scintillating fibers were excluded since they presented tilts during their insertion in the gel that affected the optical coupling to the camera, leading to large signal variations when deformed. The applied compression lead to measured dose variation between 1.66% and 5.75% (FIG. 23(a)). These dose variations present deviations of 0.8±0.7% (mean±standard deviation) from the expected variations calculated on the treatment planning system (FIG. 23(b)). In all cases, the dose differences from the treatment planning system are lower than the dose variation measured.

Thus, a real-time deformable dosimeter that can simultaneously measure dose and deformation vector fields can be developed and characterized. Its water-equivalent composition can endow it with the quality to act both as a phantom and detector. The detector can present a linear dose to signal relationship that remained when varying the dose rate or the camera's integration time. The dosimeter can accurately measure the DVF resulting from a 1 cm axial compression.

The embedded scintillating fibers can enable the measurement of dose variations resulting from the deformation of their gel matrix. Moreover, the detector can allow a wide variety of 2D and 3D geometric or anthropomorphous designs since its shape and size can be determined by the mold used to cast the urethane rubber. Such a detector could be used for the quality assurance of DIR algorithms and to explore the dosimetric impact of organ deformations.

The various embodiments described herein have been provided as examples only. It should be understood that various modifications in form and detail can be made to the embodiments described and illustrated herein, without departing from these embodiments, the scope of which is defined in the appended claims.

The invention claimed is:

1. A system for measuring radiation dose, comprising:
a radiation dosimeter;
a deforming device having a first portion and a second portion sized to receive the radiation dosimeter therebetween, at least one of the first and second portions being movable relative to the other portion to deform the radiation dosimeter;
wherein the radiation dosimeter comprises:
a phantom; and
one or more deformable radio-luminescent elements located within the phantom and configured to generate light as a direct response to irradiation, wherein the radio-luminescent elements have different optical emission spectra.

2. The system of claim 1, wherein the phantom is deformable.

3. The system of claim 1, wherein at least one radio-luminescent element is deformable.

4. The system of claim 1, wherein the radio-luminescent elements are contiguous.

5. The system of claim 1, wherein the one or more radio-luminescent elements comprise water and/or tissue equivalent materials.

6. A system for measuring radiation dose, comprising:
a radiation dosimeter;
a deforming device having a first portion and a second portion sized to receive the radiation dosimeter therebetween, at least one of the first and second portions being movable relative to the other portion to deform the radiation dosimeter;
wherein the radiation dosimeter comprises:
a structure comprising a scintillating material, wherein the scintillating material emits light when exposed to radiation; and
one or more radio-luminescent elements located within the structure and configured to generate light as a direct response to irradiation.

7. The system of claim 6, wherein the structure is deformable.

8. The system of claim 6, wherein at least one radio-luminescent element is deformable.

9. The system of claim 6, wherein the radio-luminescent elements are contiguous.

10. The system of claim 6, wherein the radio-luminescent elements have different optical emission spectra.

11. The system of claim 6, wherein the one or more radio-luminescent elements comprise water and/or tissue equivalent materials.

12. The system of claim 6, wherein the structure or the radio-luminescent elements are configured to take a shape of one of: an organ and an anatomical region.

13. The system of claim 12, wherein the anatomical region comprises any one of: a thorax, a neck, a head, and a pelvis.

14. A radiation system for real-time measurements of a radiation dose within a region, comprising:
a radiation dosimeter that comprises a structure and one or more radio-luminescent elements, wherein the structure comprises a scintillating material, the scintillating material emits light when exposed to radiation and the one or more radio-luminescent elements are located within the structure and configured to generate light as a direct response to irradiation;
a deforming device having a first portion and a second portion sized to receive the radiation dosimeter therebetween, at least one of the first and second portions being movable relative to the other portion to deform the radiation dosimeter; and
a processor configured to receive radiation data from the radiation dosimeter.

15. The radiation system of claim 14, wherein the radiation dosimeter comprises a deformable material.

16. The radiation system of claim 14 further comprising a radiation source for irradiating the radiation dosimeter.

17. The radiation system of claim 5, wherein the radiation data are recorded while the radiation dosimeter is being deformed.

18. A method for measuring a radiation dose, comprising:
positioning a radiation dosimeter for real-time measurements of the radiation dose within a deforming device having a first portion and a second portion sized to receive the radiation dosimeter therebetween, at least one of the first and second portions being movable relative to the other portion to deform the radiation dosimeter,
wherein the radiation dosimeter comprises a structure and one or more radio-luminescent elements, wherein the structure comprises a scintillating material, the scintillating material emits light when exposed to radiation and the one or more radio-luminescent elements are located within the structure and configured to generate light as a direct response to irradiation;
irradiating the radiation dosimeter;
deforming the radiation dosimeter by actuating the at least one of the first and second portions of the deforming device; and
receiving radiation data from the radiation dosimeter.

* * * * *